United States Patent
Boyd et al.

[11] Patent Number: 5,919,711
[45] Date of Patent: Jul. 6, 1999

[54] ANALYTICAL CARTRIDGE

[75] Inventors: Douglas E. Boyd, Dublin; Jan B. Yates, Reynoldsburg, both of Ohio

[73] Assignee: Careside, Inc., Culver City, Calif.

[21] Appl. No.: 08/907,426

[22] Filed: Aug. 7, 1997

[51] Int. Cl.[6] .............................. G01N 1/38; G01N 35/10
[52] U.S. Cl. ........................ 436/178; 436/45; 436/165; 436/174; 436/177; 436/179; 436/180; 422/68.1; 422/72; 422/81; 422/100; 422/101; 422/102
[58] Field of Search ................... 422/58, 61, 72, 422/81, 100, 101, 102, 68.1, 103; 436/43, 45, 164, 165, 174, 177, 178, 180, 179

[56] References Cited

U.S. PATENT DOCUMENTS

| | | | |
|---|---|---|---|
| 3,899,296 | 8/1975 | Mailen et al. | 422/72 |
| 4,708,940 | 11/1987 | Yoshida et al. | 436/45 |
| 4,740,472 | 4/1988 | Burtis et al. | 436/63 |
| 4,788,154 | 11/1988 | Guigan | 436/180 |
| 4,814,144 | 3/1989 | Edelmann et al. | 422/102 |
| 4,883,763 | 11/1989 | Holen et al. | 436/45 |
| 4,940,527 | 7/1990 | Kazlauskas et al. | 204/401 |
| 4,963,498 | 10/1990 | Hillman et al. | 436/69 |
| 5,061,381 | 10/1991 | Burd | 210/789 |
| 5,096,669 | 3/1992 | Lauks et al. | 422/61 |
| 5,122,284 | 6/1992 | Braynin et al. | 210/782 |
| 5,147,607 | 9/1992 | Mochida | 422/57 |
| 5,160,702 | 11/1992 | Kopf-Sill et al. | 422/72 |
| 5,171,533 | 12/1992 | Fine et al. | 422/72 |
| 5,186,844 | 2/1993 | Burd et al. | 210/782 |
| 5,242,606 | 9/1993 | Braynin et al. | 210/787 |
| 5,275,016 | 1/1994 | Chatterjee et al. | 62/381 |
| 5,286,454 | 2/1994 | Nilsson et al. | 422/102 |
| 5,288,463 | 2/1994 | Chemelli | 422/58 |
| 5,304,348 | 4/1994 | Burd et al. | 422/72 |
| 5,399,486 | 3/1995 | Cathey et al. | 435/7.9 |
| 5,403,415 | 4/1995 | Schembri | 156/73.1 |
| 5,409,665 | 4/1995 | Burd | 422/64 |
| 5,413,732 | 5/1995 | Buhl et al. | 252/182.11 |
| 5,416,026 | 5/1995 | Davis | 436/66 |
| 5,427,915 | 6/1995 | Ribi et al. | 435/7.92 |
| 5,447,440 | 9/1995 | Davis et al. | 435/6 |
| 5,449,621 | 9/1995 | Klein | 436/45 |
| 5,457,053 | 10/1995 | Burd et al. | 436/45 |
| 5,472,063 | 12/1995 | Schembri | 210/380.1 |
| 5,472,671 | 12/1995 | Nilsson et al. | 422/102 |
| 5,478,750 | 12/1995 | Bernstein et al. | 436/164 |
| 5,500,187 | 3/1996 | Deoms et al. | 422/58 |
| 5,503,985 | 4/1996 | Cathey et al. | 435/7.9 |
| 5,589,399 | 12/1996 | Allen et al. | 436/169 |

FOREIGN PATENT DOCUMENTS

| | | |
|---|---|---|
| 0 160 282 B1 | 1/1990 | European Pat. Off. . |
| 0 397 424 A2 | 11/1990 | European Pat. Off. . |
| 0 407 827 A2 | 1/1991 | European Pat. Off. . |
| 0 430 248 A2 | 6/1991 | European Pat. Off. . |
| 0 318 255 B1 | 4/1993 | European Pat. Off. . |
| 0 381 501 B1 | 6/1994 | European Pat. Off. . |
| 0 470 202 B1 | 6/1994 | European Pat. Off. . |
| 0 482 721 B1 | 9/1995 | European Pat. Off. . |
| 0 550 090 B1 | 9/1996 | European Pat. Off. . |
| 82 06036 | 4/1982 | France . |
| WO 90/13016 | 11/1990 | WIPO . |
| WO/96/06354 | 2/1996 | WIPO . |

*Primary Examiner*—Long V. Le
*Attorney, Agent, or Firm*—Oppenheimer Wolff & Donnelly LLP

[57] ABSTRACT

An analytical cartridge adapted for use in analyzing fluids which contain liquid and solid components. The cartridge includes a plumbing system composed of various wells or chambers which are interconnected by passageways. After introduction into the cartridge, liquid samples are separated and transported to a test well utilizing a sequential application of centrifugal force followed by pressurization of the system. The cartridge may be used to measure the concentration of a wide variety of chemical constituents in bodily fluids and is useful in measuring other properties of these fluids which contain liquid and solid components.

20 Claims, 5 Drawing Sheets

ANALYTICAL CARTRIDGE

BACKGROUND OF THE INVENTION

1. Field of the Invention

The present invention relates generally to systems and methods which are used in the analysis of multi-component fluids which contain both liquid and solid components. More particularly, the present invention relates to the instrumentation and methods which are used in clinical laboratories and other healthcare locations to analyze blood and other bodily fluids.

2. Description of the Related Art

Clinical chemistry involves the qualitative and quantitative analyses of body fluids, such as blood, urine, spinal fluid and other materials. Clinical chemistry encompasses multiple specialty testing areas including coagulation, hematology, immunochemistry, as well as chemistry. The test results derived from such analyses are used by physicians and other healthcare professionals to diagnose, monitor and treat diseases. The analysis protocols, instrumentation and other equipment utilized in clinical laboratory testing must be capable of providing accurate and repeatable test results. In addition, it is desirable that the procedures and instrumentation be simple and efficient. The testing equipment and procedures should be versatile enough that they can be used in healthcare locations where relatively few samples are tested as well as in larger clinical laboratories where the number of samples being tested on a daily basis is quite large.

Another consideration in designing analytical equipment for use by healthcare personnel is the amount of sample available for testing. In many situations, the amount of blood or other bodily fluid available is relatively small. Accordingly, there has been a trend in clinical chemistry to develop analytical systems which are capable of conducting numerous different chemical analyses on relatively small amounts of sample. In general, the goal has been to develop clinical analytical systems which provide the maximum number of medical tests utilizing the minimum amount of sample.

In achieving the above goals, a multitude of different analytical procedures and approaches have been investigated. In one approach, instruments have been developed which have a single sample introduction site. The equipment is designed so that the sample is split and routed to various locations within the system where multiple chemical analyses take place. Other systems do not include internal sample splitting devices and rely on the clinical chemist to separate the sample into small aliquots which are introduced into various instruments which are capable of conducting a maximum of only a few chemical analyses at one time.

There is a continuing need to develop and provide clinical chemistry equipment which is not only accurate, but versatile enough to meet the demands of modern medicine. The equipment should be simple enough to be used by not only highly-skilled laboratory technicians, but also by other healthcare personnel who may be required to conduct laboratory tests from time to time. The equipment and procedures should be versatile enough so that they can be utilized in clinical laboratories which analyze thousands of samples daily, while at the same time being adaptable to doctors' offices, home healthcare agencies and nursing homes where the number of tests being conducted is not as great. In addition, the equipment should be versatile enough to be useful in conducting a wide variety of blood analyses which are presently being routinely utilized. In addition, the equipment should be adaptable to conducting blood or other bodily fluid tests which will be developed in the future.

SUMMARY OF THE INVENTION

In accordance with the present invention, an analytical cartridge is provided which can be used in a centrifuge-based system for analyzing a wide variety of biological fluids. The analytical cartridge is especially adapted for analyzing fluids, such as blood, which contain both liquid and solid components. The cartridge includes a test well which can be adapted to carry out a wide variety of clinical tests including a multitude of chemistry, coagulation, electrochemistry and immuno-chemistry tests.

The analytical cartridge in accordance with the present invention is composed of a housing which includes a cartridge body having a top surface, bottom surface and outer walls defining a housing perimeter. The cartridge body further includes an inner end and an outer end. Within the housing body is located a deposition well which is designed to receive solutions, such as blood and other bodily fluids, which contain liquid and solid components. The cartridge further includes a separation well located at a position which is more towards the outer end of the cartridge body than the deposition well. An overflow well is also located in the cartridge body at a position which is more towards the outer end of the cartridge body than the deposition well. A test well is located in the cartridge body at a position which is more towards the inner end of the cartridge body than the separation well.

The various wells located within the cartridge body are connected together by way of an inlet passageway between the deposition well and separation well, an outlet passageway located between the separation well and test well, and an overflow passageway located between the separation well and overflow well. As a feature of the present invention, a pressurization device is provided which provides selective pressurization of the deposition well to provide controlled movement of liquid within the cartridge body. During operation, blood or other liquid which may contain solid components is introduced into the deposition well. The analytical cartridge is then centrifuged or otherwise subjected to centrifugal force which moves the solution from the deposition well to the separation well and overflow well, if necessary. During the centrifugation, the solution is separated, if necessary, into solid components located in the separation well and substantially solids-free liquid located in the inlet passageway, outlet passageway, and overflow passageway (if necessary). Once centrifuging is complete, the test well is pressurized to provide flow of the solids-free liquid from the inlet and outlet passageways into the test well. Once in the test well, the solids-free liquid is tested utilizing conventional clinical procedures.

The analytical cartridge in accordance with the present invention is well-suited for use in a wide variety of clinical settings. Numerous different clinical analyses may be carried out utilizing the cartridge by merely modifying the reagents or other test elements located in the test well. This allows the healthcare personnel to conduct a wide variety of different analyses on a given sample by selecting the appropriate cartridges.

The above described and many other features and attendant advantages of the present invention will become better understood by reference to the following detailed description when taken in conjunction with the accompanying drawings.

DETAILED DESCRIPTION OF THE INVENTION

Figure 1:
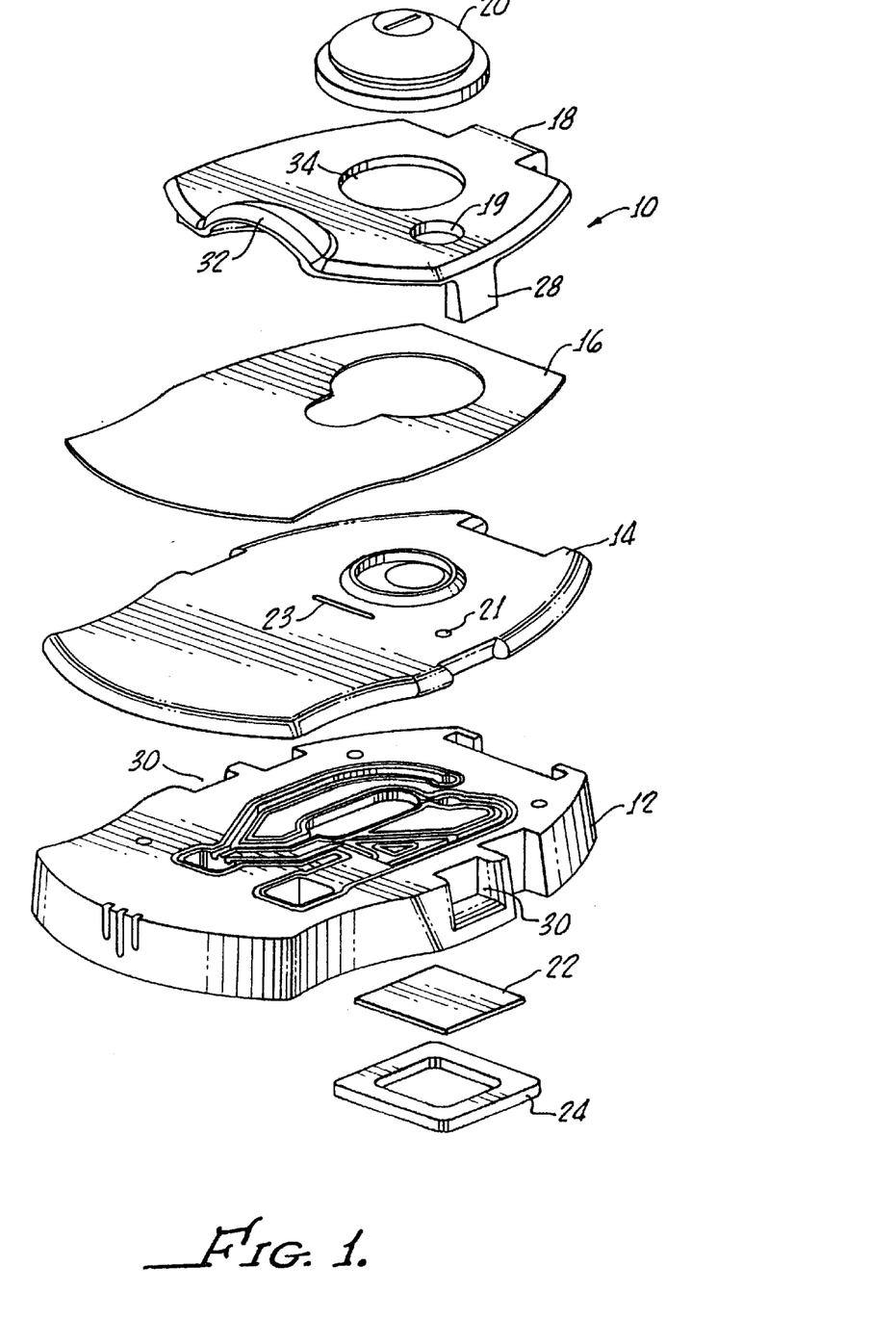
FIG. 1 is an exploded view of a preferred exemplary analytical cartridge in accordance with the present invention.
Figure 2:
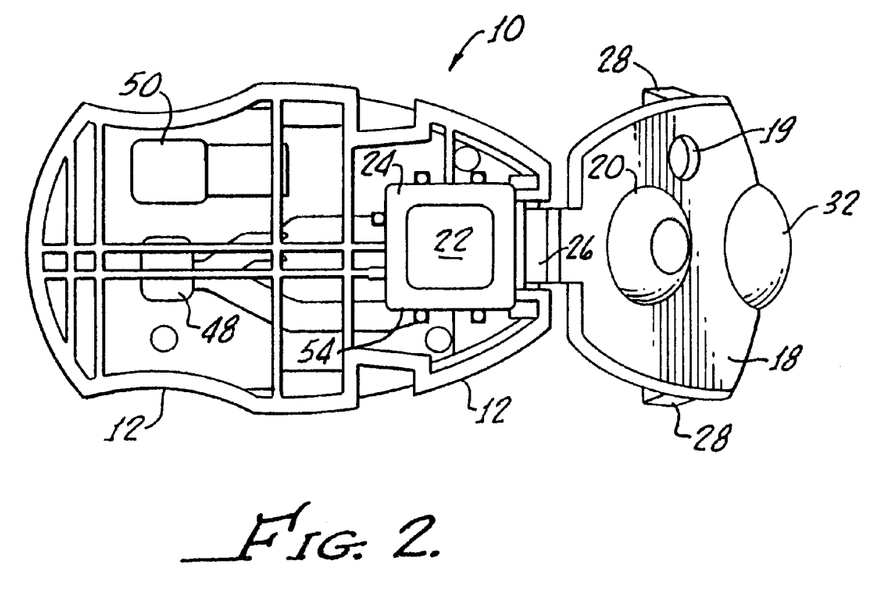
FIG. 2 is a bottom view of the analytical cartridge shown in FIG. 1.
Figure 3:
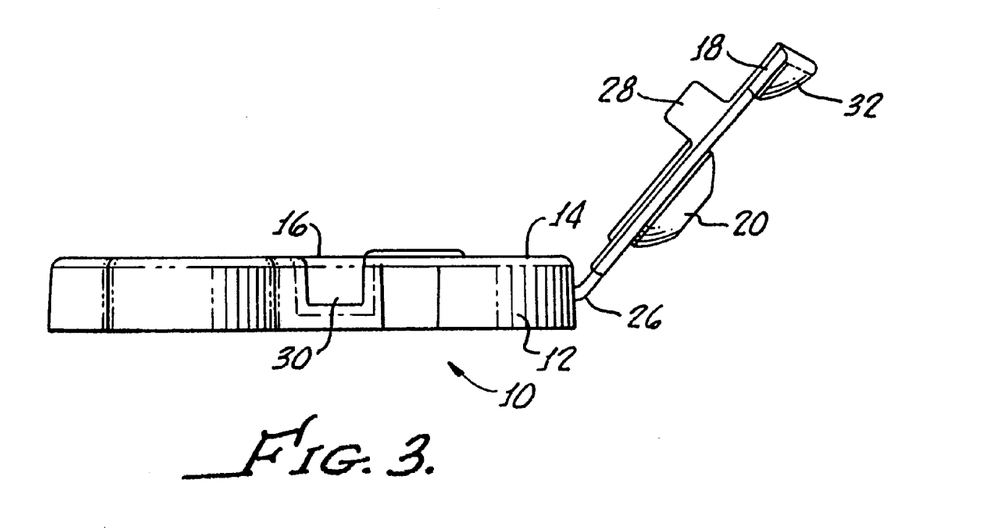
FIG. 3 is a side view of the analytical cartridge shown in FIG. 2.

A preferred exemplary analytical cartridge in accordance with the present invention is shown generally at 10 in FIGS. 1–3. The cartridge 10 is made up of a housing which includes a cartridge body 12, top plate 14 and label 16. The analytical cartridge 10 further includes a hinged cap 18, flexible septum 20, reagent film 22, and retainer ring 24. In FIGS. 2 and 3, the analytical cartridge 10 is shown, as assembled, from a bottom and side view, respectively. As best shown in FIGS. 2 and 3, the cap 18 is preferably hinged to the cartridge body 12 as shown at 26. The cap 18 includes locking tabs 28 which are designed to releasably engage indentations 30 in the cartridge body 12. The cap 18 preferably includes a curved portion 32 which provides access under the cap 18 so that it can be easily opened and closed. The cap 18 and top plate 14 have vent holes 19 and 21, respectively. The cartridge body 12 and top plate 14 are preferably made from a suitable plastic, such as polystyrene, polyvinylchloride, polycarbonate, or any other plastic which is rigid and inert with respect to biological fluids. Hinged cap 18 is preferably made from a suitable plastic, such as polypropylene or polyethylene or any other plastic which is flexible and inert with respect to biological fluids.

The septum 20 is shaped to fit within opening 34 in the cap 18. The septum must be shaped to provide a sealing engagement with the cap 18 and top plate 14 so that depression of the septum 20 when the cap 18 is closed onto the top plate 14 results in pressure being applied to the cartridge body as will be described in more detail below. The septum 20 is made from an elastomeric material such as silicone rubber or any other elastomeric material that is inert with respect to biological fluids. The label 16 is optional and may be made from any of the well-known label materials conventionally used to allow writing onto laboratory equipment. Preferably, the label will be of the self-adhesive variety. The label 16 will preferably include an identification of the cartridge test chemistry along with instructions or other notes, such as a bar code, relevant to the specific test protocol.

Figure 4:
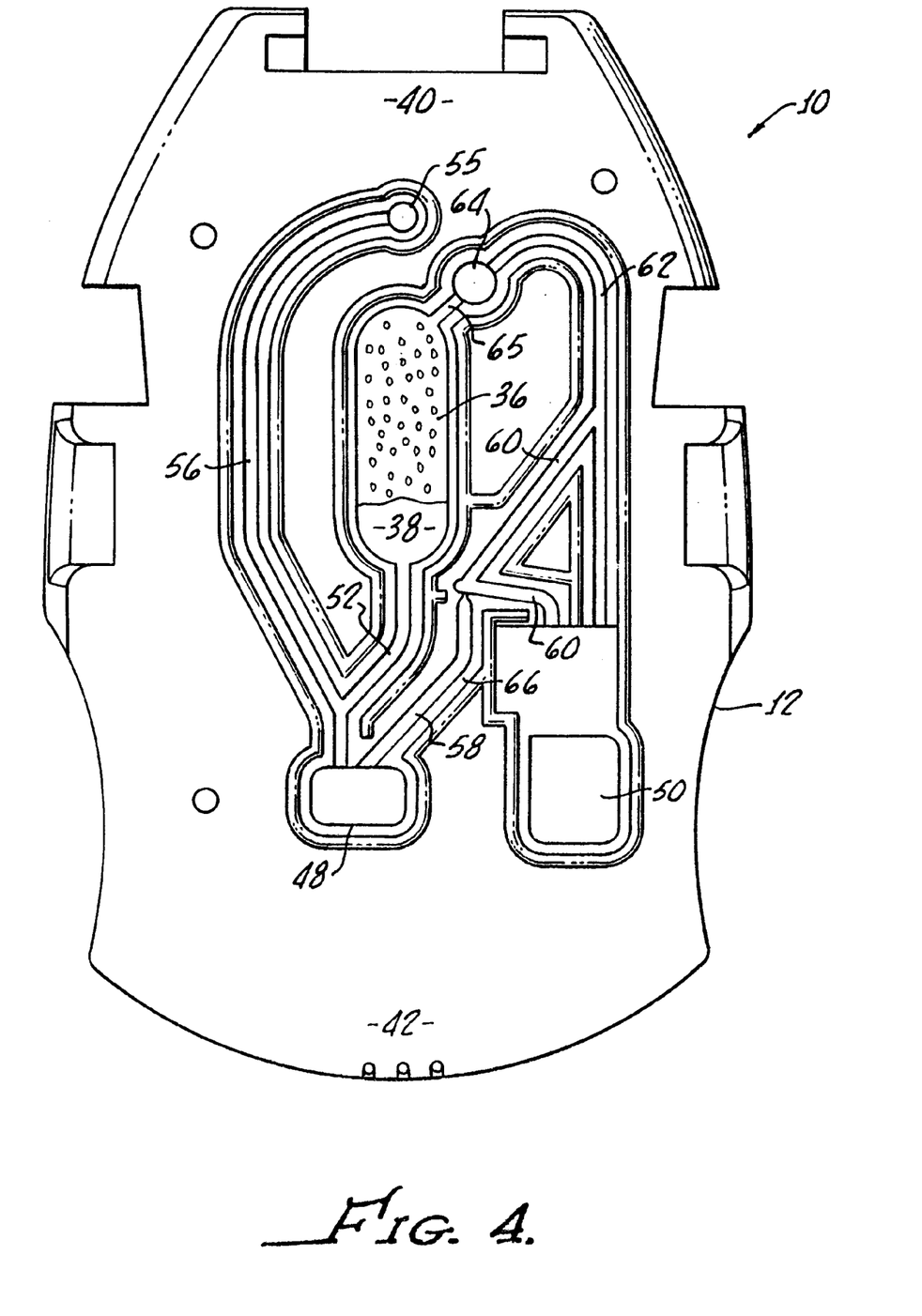
FIG. 4 is a top view of the cartridge body depicting the first step of a preferred analytical procedure wherein a blood sample has been introduced into the deposition well.
Figure 5:
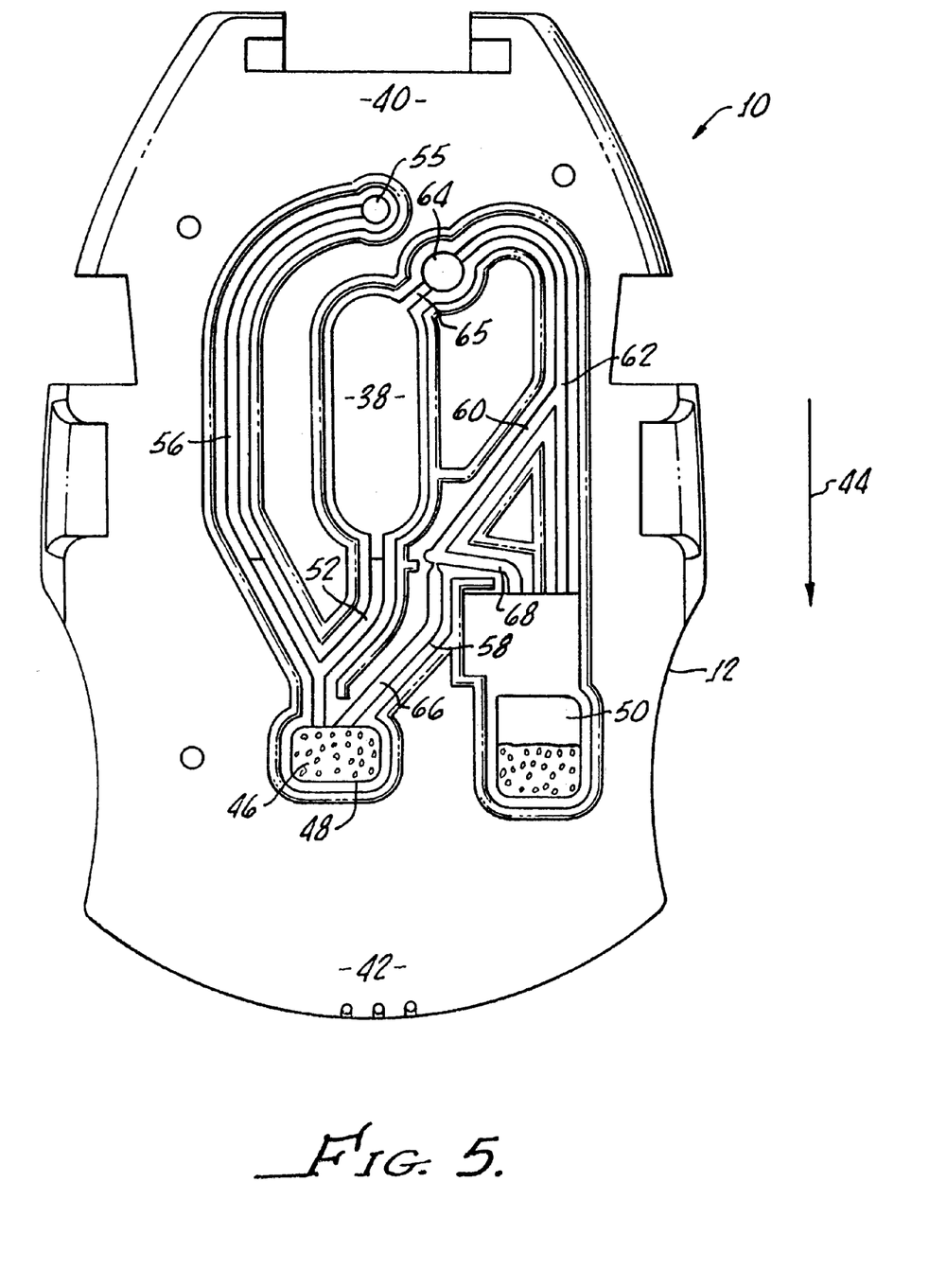
FIG. 5 depicts the cartridge body after it has been subjected to centrifugation in order to concentrate the red and white blood cells in the separation well.
Figure 6:
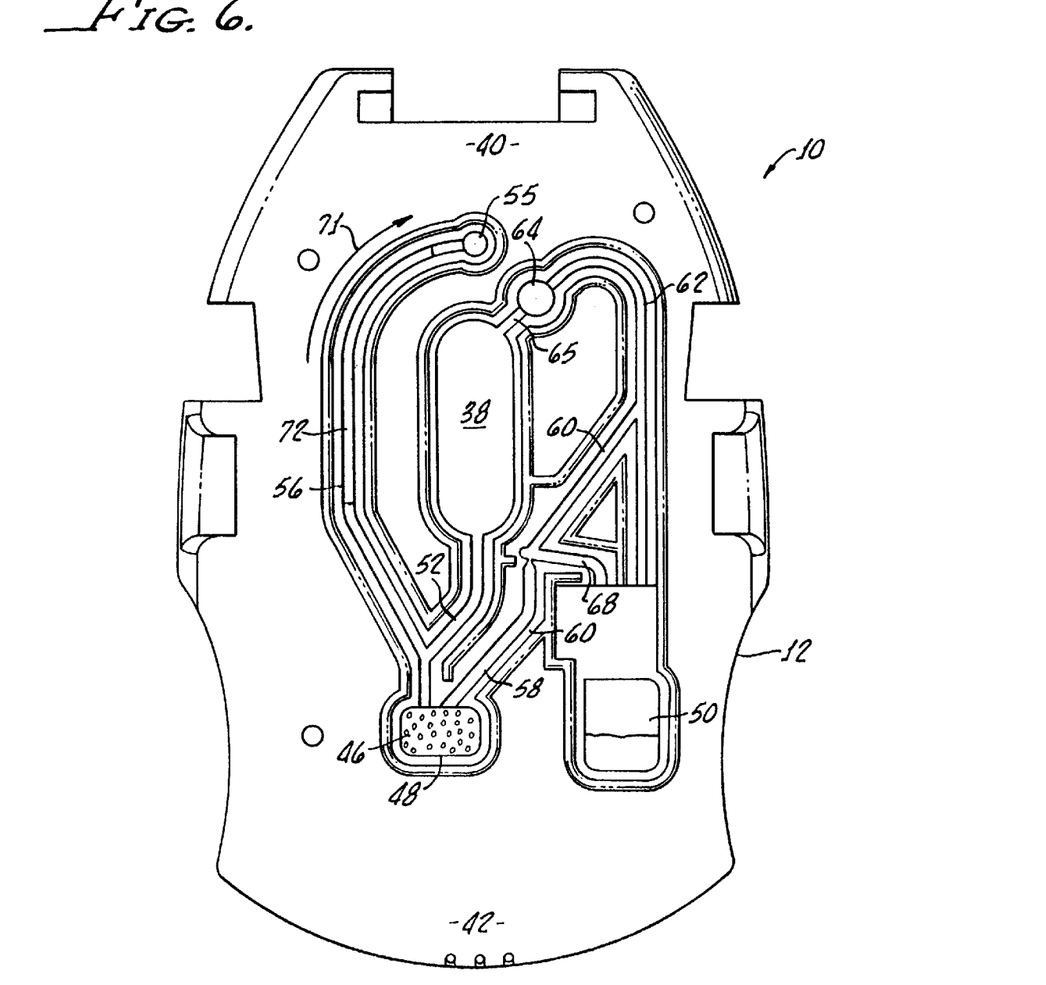
FIG. 6 is a view of the cartridge body depicting the transfer of cell-free liquid to the test well during pressurization of the deposition well.

FIGS. 4–6 are top views of the cartridge body 12 showing a preferred exemplary test cartridge at various stages during the testing procedure. Referring to FIG. 4, the test cartridge 12 is shown during the first step of the analytical process where a blood sample 36 is located in deposition well 38. The cartridge body 12, as shown in FIG. 4, has an inner end 40 and an outer end 42. After the blood sample 36 has been deposited in deposition well 38, the cartridge cap 18 is closed and the cartridge is placed in a centrifuge or other apparatus which is capable of causing the blood sample 36 to be transferred towards the outer end 42 as indicated by arrow 44 (see FIG. 5). Preferably, the centrifuge apparatus will be designed to house multiple cartridges which can be centrifuged simultaneously.

The top plate 14 includes a window 23 which provides visual access to the deposition well 38. The window 23 may be clear or opaque. If opaque, the window 23 must be sufficiently transparent to allow one to visually assess the contents of the deposition well 38. The window 23 is preferably in the shape of narrow strip as shown in FIG. 1. The window strip 23 is positioned so that blood or other sample only becomes visible when the required amount of sample has been deposited into the well 38. The window 23 allows the operator to quickly and accurately verify that the appropriate amount of sample has been deposited. Other types of detection systems may be used to verify filling of the deposition well. However, the use of a window, such as window strip 23, is preferred due to its simplicity.

As shown in FIG. 5, sufficient centrifugal force is applied to the cartridge 10 to ensure that the blood cells as shown at 46 are concentrated in separation well 48. The size of the deposition well 38 is chosen to allow deposition of an excess of sample. As a result, an overflow well 50 is provided. A detector (not shown) may be provided to detect when fluid reaches the overflow well 50. The detector is provided to insure that adequate sample has been introduced into the cartridge. The detector is preferably connected to a control system which nullifies the test if sufficient sample is not initially loaded into the cartridge to provide flow into the overflow well 50 as measured by the detector. The detector can be a simple visual detector like the window strip 23 described above. The detector could also be a more complicated system utilizing detector electrodes or the like to provide an electronic signal when fluid reaches the overflow well 50.

As shown in FIG. 5, the deposition well 38 is connected to the separation well 48 by inlet passageway 52. The separation well 48 is connected to test well 54 by way of outlet passageway 56. Also, the separation well 48 is connected to the overflow well 50 by way of overflow passageway 58. Vent passageways 60 and 62 are connected to vent opening 21 in top plate 14 to allow liquids to be transferred through the various passageways to the various wells without the build-up of back pressure. Vent passageway 62 is connected to the deposition well 38 by way of a capillary break zone 64 and vent leg 65. The capillary break zone 64 is designed to prevent inadvertent capillary flow of fluid from the deposition well 38 through passageway 62. The particular shape of capillary break zone 64 is not critical provided that their is a sufficient increase in relative opening size between the capillary break zone 64 and the vent leg 65 to prevent capillary action from transporting fluid from the vent leg 65 to the vent passageway 62.

As shown in FIG. 5, centrifuging of the analytical cartridge 10 results in the separation of the blood plasma from a solid or cellular component located in separation well 48 and any overflow located in overflow well 50. Substantially solids-free plasma remains in portions of the outlet passageway 56, inlet passageway 52, and overflow passageway 58 as shown in the shaded portions in FIG. 5. The speed at which the cartridge 10 is centrifuged, as well as the time, may be varied depending upon a number of different criteria. For example, in many situations it is not necessary or desirable to separate cells or other components from the sample fluid. In these cases, the centrifuge time and/or speed are kept at sufficiently low levels to provide flow of fluid into the passageways and separation well, as described above, without separating the solid components from the fluid. The result is an accurately metered homogeneous sample.

The optimum centrifuge speed and time can be determined by routine experimentation as is well known in the art. The centrifuge load should be on the order of 200 to 400 g's with centrifuge times ranging from about 1 to 10 minutes and a time to speed of less than 3 or 4 seconds. When cell separation and removal is desired, the centrifuge parameters are chosen so that substantially all of the cellular components of the blood are separated out, leaving a substantially solids-free liquid located in the passageways as shown in FIG. 5. In situations where the sample is to be metered only and not separated, it is preferred to keep the centrifuge load relatively high. Separation is prevented from occurring by substantially reducing the centrifuge time.

Referring again to FIG. 5, the amount of substantially solids-free liquid which remains in the inlet passageway 52 and outlet passageway 56 is determined by the sizes of passageways 52 and 56 and the configuration of overflow passageway 58. The overflow passageway 58 is preferably composed of a separation well segment 66 and an overflow well segment 68. The separation well segment 66 includes a first end that is connected to the separation well 48 and a second end which is connected to the overflow well segment 68. The overflow well segment 68 has a first end which is connected to the separation well segment 66 and a second end which is connected to the overflow well 50. The connection point between the separation well segment 66 and overflow well segment 68 is shown in detail in FIGS. 7 and 8. The separation well segment 66 forms an upstream passageway in the overflow passageway 58 which has a restriction 70 at its upstream or second end. The restriction 70 has a cross-sectional area which is substantially smaller than the cross sectional area of the upstream passageway or separation well segment 66 at its first end which is connected to the separation well 48. This reduction in cross-sectional area as shown at 70 is required to ensure that capillary action does not adversely affect the metering process and aliquotting of liquid in the inlet passageway 52 and outlet passageway 56. It is also preferred that the cross-sectional area of the separation well segment at 70 be less than the cross-sectional area of the overflow well segment 68. This configuration is preferred in order to provide a break in possible unwanted capillary action within the various passageways and wells. It is also preferred that the connection between the separation well segment 66 and overflow well segment 68 be vertically offset as shown in FIG. 8. The configuration shown in FIGS. 7 and 8 for providing a capillary break is preferred. Other configurations are possible provided that relative changes in cross-sectional areas and the orientation of the connection point between the upstream and downstream portions of the overflow passageway 58 are such that capillary induced flow is prevented.

Figure 7:
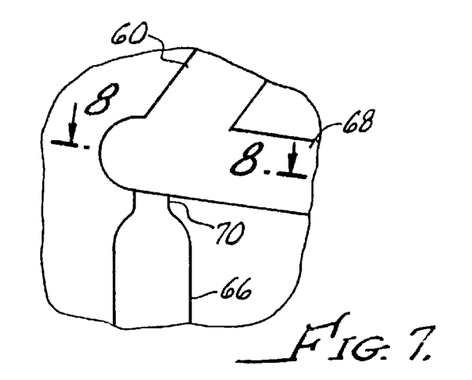
FIG. 7 is a detailed view of the portion of the overflow passageway showing the connection between the separation well segment of the passageway and the overflow well segment.
Figure 8:
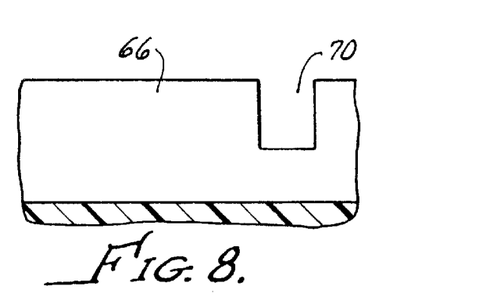
FIG. 8 is a sectional view of FIG. 7.

Preferably, the reduction in cross-sectional area shown as constriction 70 in FIG. 7 will occur adjacent to the connection with the overflow well segment 68. Preferably, the separation well segment 66 will be a channel having widths of between 0.7 and 1.1 mm and depths of between about 0.1 and 0.2 mm. The constriction 70 will have widths on the order of 0.3 to 0.5 mm and depths on the order of 0.1 to 0.2 mm. The overflow well segment 68 and the remainder of the various passageways are preferably channels also having the above widths, but depths on the order of 0.5 and 1.5 mm. It is particularly preferred that the channel dimensions for all of the passageways (inlet passageway 52, outlet passageway 56, overflow passageway 58, ventline 60 and 62) all be on the order of 0.8 mm wide by 1.1 mm deep. The preferred dimensions for the constriction 70 is 0.4 mm wide by 0.1 mm deep. Passageways having cross-sectional configurations other than square or rectangular channels are possible.

After completion of the centrifuging step, the substantially solids-free liquid located in the inlet passageway 52 and outlet passageway 56 are transported through the outlet passageway 56 as represented by arrow 71 in FIG. 6. The liquid as shown at 72 is forced towards the test well 54 by pressure which is applied to deposition well 38 by compressing septum 20. Although it is possible to move liquid 72 into test well 54 by pressing septum 20 by hand, it is preferred that an automatic system be utilized wherein multiple cartridges 10 are centrifuged simultaneously and then an apparatus be provided which automatically presses down on septum 20 to provide desired pressurization of deposition well 38 to force the liquid 72 into test well 54. The vent 21 in the cover 14 must be sealed when the system is pressurized using septum 20.

As best shown in FIG. 2, it is preferred that the test well 54 be located towards the bottom of the cartridge. In FIGS. 4–6, the entry to the test well is also shown at 55. The test well 54 is preferably larger than the opening shown at 55 and is located within the cartridge body 12. In a preferred exemplary embodiment, a reagent film 22 is placed at the bottom of the test well 54. Different reagent films are available for testing different chemical substances in blood. The particular reagent film utilized in the test cartridge will depend upon the blood component being measured. Reagent films which are capable of providing sensitive and specific measurement of a wide variety of blood and urine chemistries are available. For example, reagent films are commercially available from Johnson & Johnson Clinical Diagnostics (100 Indigo Creek Drive, Rochester, N.Y. 14650) and Fuji Photo Film Co., Ltd. (26–30 Nishiazabu 2-chome, Minato-ku, Tokyo, Japan). For example, reagent films are available for testing glucose, calcium, cholesterol, total bilirubin, hemoglobin, uric acid, ammonia, AST, GGT, LDH, ALT, LAP, amylase, alkaline phosphatase, creatine kinase, total calcium, triglycerides, cholesterol, HDL cholesterol, glucose, total protein, albumin, creatinine, urea nitrogen, inorganic phosphorus, magnesium, carbon dioxide, ionized calcium, sodium, potassium, and chloride.

The majority of reagent films change color or exhibit some type of measurable change which can be detected utilizing conventional instrumentation such as relectometers, photometers, fluorometers, specialized electrode detectors, and the like. In addition to reagent films, various other measurement systems may be incorporated into the test well. Systems for measuring blood coagulation and immunoassays are possible. The various conventional reagents and detectors utilized in the various blood chemistries are well-known and can be utilized in connection with the test well. Basically, any blood measurement protocol wherein plasma/serum is subjected to chemical treatment and/or measurement within a relatively small test vessel may be utilized. The size of the test well 54 in the cartridge body 12 will range in volume from 0.005 ml to 0.1 ml.

Although this preferred exemplary embodiment is being described with respect to the use of reagent films used in combination with a suitable detector, it will be understood by those skilled in the art that many other reagent and detection systems are possible. In this regard, it will also be apparent to those of ordinary skill in the art that many additional embodiments of the present invention are possible. For example, multiple test wells may be included in the cartridge body to provide multiple simultaneous analyses in a single analytical cartridge.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. An analytical cartridge adapted for use in analyzing fluids which contain liquid and solid components, said cartridge comprising:

a housing comprising a cartridge body which has a top surface, bottom surface and outer walls defining a housing perimeter, said body further comprising an inner end and an outer end;

a deposition well located in said cartridge body for receiving fluids which contain liquid and solid components;

a separation well located in said cartridge body at a position which is more towards said outer end than said deposition well;

an inlet passageway in said cartridge body which connects said deposition well to said separation well;

a test well located in said cartridge body at a position which is more towards said inner end than said separation well;

an outlet passageway in said cartridge body which connects said separation well to said test well;

an overflow well located in said cartridge body at a position which is more towards said outer end than said deposition well or test well;

an overflow passageway in said cartridge body which connects said separation well to said overflow well; and a pressurization device for pressurizing said deposition well to provide controlled movement of solution within said cartridge body.

2. An analytical cartridge according to claim 1 wherein said pressurization device comprises a flexible septum which can be moved from a relaxed position to one or more compressed positions, wherein movement from said relaxed position to said one or more compressed positions provides pressurization of said deposition well.

3. An analytical cartridge according to claim 2 wherein said septum is located in a cap, said cap being movable between an open position wherein said septum is displaced away from said deposition well to allow introduction of solution into said deposition well and a closed position wherein said septum is in a position to provide pressurization of said deposition well.

4. An analytical cartridge according to claim 3 wherein said cap comprises a first end and a second end wherein said cap is hinged to said cartridge body at either said first or second end.

5. An analytical cartridge according to claim 1 wherein said overflow passageway comprises:

a separation well segment which extends between a first end that is connected to said separation well and a second end, said separation well segment defining an upstream passageway which has a cross-sectional area at said second end which is smaller than the cross-sectional area of said upstream passageway at said first end; and an overflow well segment which extends between a first end and a second end wherein said second end is connected to said overflow well, said overflow well segment defining a downstream passageway which has a cross-sectional area at said first end which is greater than the cross-sectional area of said upstream passageway at said second end and wherein the second end of said separation well segment is connected to the first end of said overflow well segment to provide fluid transport between said separation well segment and said overflow well segment.

6. An analytical cartridge according to claim 5 wherein said first end of said overflow well segment comprises a wall and wherein said second end of said separation well segment is connected to said overflow well segment at said wall wherein said connection defines an opening in said wall which communicates between said upstream passageway and said downstream passageway.

7. An analytical cartridge according to claim 5 which further comprises a vent passageway having a first end connected to the overflow well segment to said overflow well passageway.

8. An analytical cartridge according to claim 7 wherein said vent passageway comprises a second end connected to said deposition well and wherein a capillary break zone is located at said second end of said vent passageway.

9. An analytical cartridge according to claim 5 wherein said separation well segment of said overflow passageway comprises a constriction at said second end where said upstream passageway connects to said downstream passageway.

10. An analytical cartridge according to claim 1 wherein said cartridge further comprises one or more reagents located in said test well which are capable of interacting with said fluid to provide a measurable result.

11. An analytical cartridge according to claim 10 wherein said one or more reagents are in the form of a film located on a support surface.

12. A method for analyzing a fluid which contains solid and/or liquid components, said method comprising the steps of:

a) introducing said fluid into an analytical cartridge wherein said cartridge comprises:

a housing comprising a cartridge body which has a top surface, bottom surface and outer walls defining a housing perimeter, said body further comprising an inner end and an outer end;

a deposition well located in said cartridge body for receiving fluids which contain liquid and solid components;

a separation well located in said cartridge body at a position which is more towards said outer end than said deposition well;

an inlet passageway in said cartridge body which connects said deposition well to said separation well;

a test well located in said cartridge body at a position which is more towards said inner end than said separation well;

an outlet passageway in said cartridge body which connects said separation well to said test well;

an overflow well located in said cartridge body at a position which is more towards said outer end than said deposition well or test well;

an overflow passageway in said cartridge body which connects said separation well to said overflow well;

a pressurization device for pressurizing said deposition well to provide controlled movement of fluid with said cartridge body, wherein said fluid is introduced into said deposition well in an amount which is sufficient to at least partially fill said deposition well;

b) centrifuging said analytical cartridge with said inner end and outer end of said cartridge body oriented so that said fluid flows through said inlet passageway to said separation well, said analytical cartridge being centrifuged for a sufficient time and at a sufficient centrifugal force to transport said fluid into said separation well, said inlet passageway, said outlet passageway and said overflow passageway;

c) pressurizing said test well to provide flow of fluid from said inlet and outlet passageways into said test well; and d) analyzing said fluid in said test well.

13. A method according to claim 12 wherein said fluid comprises both solid and liquid components and wherein said analytical cartridge is centrifuged for a sufficient time and at a sufficient centrifugal force to separate said fluid into solid components located in said separation well and substantially solids-free liquid located in said inlet passageway, outlet passageway and overflow passageway.

14. A method according to claim 12 wherein said step of analyzing said liquid in said test well comprises contacting said liquid with a reagent and measuring the interaction between said reagent and said liquid.

15. A method according to claim 14 wherein said reagent is in the form of a film which is located on a support surface.

16. A method according to claim 12 wherein said fluid which is analyzed is blood, said blood being separated during said centrifuging step into a cell fraction located in said separation well and a cell-free liquid which contains chemical components and has coagulation properties and wherein said cell-free liquid is analyzed in said test well.

17. A method according to claim 16 wherein said step of analyzing said cell-free liquid comprises measuring the coagulation properties of said cell-free liquid.

18. A method according to claim 16 wherein said step of analyzing said cell-free liquid comprises measuring the electrolyte properties of said cell-free liquid.

19. A method according to claim 16 wherein said step of analyzing said cell-free liquid comprises testing said liquid for the presence of one or more of said chemical components.

20. An analytical cartridge adapted for use in analyzing fluids, said cartridge comprising:

a housing comprising a cartridge body which has a top surface, bottom surface and outer walls defining a housing perimeter, said body further comprising an inner end and an outer end;

a deposition well located in said cartridge body for receiving fluids which contain liquid and solid components;

a metering system located in said cartridge body at a position which is more towards said outer end than said deposition well;

a test well located in said cartridge body at a position which is more towards said inner end than said deposition well;

an overflow well located in said cartridge body at a position which is more towards said outer end than said deposition well or test well;

a passageway in said cartridge body which connects said deposition well to said test well and said overflow well; and a pressurization device for pressurizing said deposition well to provide controlled movement of solution within said cartridge body.

* * * * *